United States Patent
Bowman

(10) Patent No.: US 10,052,064 B2
(45) Date of Patent: Aug. 21, 2018

(54) EDEMA MONITOR

(71) Applicant: H. Frederick Bowman, Needham, MA (US)

(72) Inventor: H. Frederick Bowman, Needham, MA (US)

(73) Assignee: Thermal Technologies, Inc., Waltham, MA (US)

( * ) Notice: Subject to any disclaimer, the term of this patent is extended or adjusted under 35 U.S.C. 154(b) by 148 days.

(21) Appl. No.: 13/999,906

(22) Filed: Apr. 1, 2014

(65) Prior Publication Data

US 2014/0303513 A1 Oct. 9, 2014

Related U.S. Application Data

(60) Provisional application No. 61/853,421, filed on Apr. 4, 2013.

(51) Int. Cl.
*A61B 5/00* (2006.01)
*A61B 5/01* (2006.01)
*A61B 5/03* (2006.01)

(52) U.S. Cl.
CPC .............. *A61B 5/4878* (2013.01); *A61B 5/01* (2013.01); *A61B 5/031* (2013.01); *A61B 5/4064* (2013.01); *A61B 5/6864* (2013.01)

(58) Field of Classification Search
CPC ............................ A61B 5/4878; A61B 5/4875
USPC .......................................................... 600/549
See application file for complete search history.

(56) References Cited

U.S. PATENT DOCUMENTS

| | | | |
|---|---|---|---|
| 4,676,252 A | 6/1987 | Trautman et al. | |
| 4,852,027 A | 7/1989 | Bowman et al. | |
| 5,005,582 A | 4/1991 | Serikov et al. | |
| 5,453,576 A | 9/1995 | Krivitski | |
| 6,488,677 B1 | 12/2002 | Bowman et al. | |
| 6,537,230 B1 | 3/2003 | Pfeiffer et al. | |
| 6,950,699 B1 | 9/2005 | Manwaring et al. | |
| 7,033,321 B1 | 4/2006 | Sarvazyan | |
| 7,239,902 B2 | 7/2007 | Schmitt et al. | |
| 7,632,235 B1 * | 12/2009 | Karicherla ............. | A61B 5/028 600/454 |
| 7,643,858 B2 | 1/2010 | Agashe et al. | |
| 7,657,292 B2 | 2/2010 | Baker et al. | |
| 7,666,146 B2 | 2/2010 | Pfeiffer et al. | |
| 8,295,920 B2 | 10/2012 | Bouton et al. | |
| 8,359,093 B2 | 1/2013 | Wariar | |

(Continued)

FOREIGN PATENT DOCUMENTS

| | | |
|---|---|---|
| WO | WO-2007-036586 | 4/2007 |
| WO | WO-2012-130249 | 3/2012 |

OTHER PUBLICATIONS

Sang-Bae Ko et al. Real Time Estimation of Brain Water Content in Comatose Patients Ann Neurol. Sep. 2012; 72(3): 344-350.*

*Primary Examiner* — Michael C Stout
(74) *Attorney, Agent, or Firm* — James L. Neal

(57) ABSTRACT

An edema monitor uses patient-specific measurements of tissue conductivity and tissue perfusion and an empirically developed perfusion coefficient of thermal conductivity to obtain tissue intravascular water and tissue extravacular water components of tissue total water. Edema is an excess of tissue extravacular water. A value for edema is obtained by deducting from the obtained value for tissue extravacular water a normal value for tissue extravacular water.

4 Claims, 8 Drawing Sheets

(56) References Cited

U.S. PATENT DOCUMENTS

| | | |
|---|---|---|
| 2007/0073180 A1 | 3/2007 | Bohn et al. |
| 2010/0234716 A1 | 9/2010 | Engel |
| 2011/0105911 A1* | 5/2011 | Borg ............... A61B 5/028 600/481 |
| 2012/0190991 A1* | 7/2012 | Bornzin ............ A61B 5/0215 600/485 |
| 2014/0081157 A1* | 3/2014 | Joeken ............. A61B 5/028 600/484 |

* cited by examiner

EDEMA MONITOR

PRIORITY CLAIM

This application claims priority from commonly owned U.S. Provisional Application Ser. No. 61/853,421, filed Apr. 4, 2013, the disclosure of which is incorporated herein by reference.

BACKGROUND OF THE INVENTION

Edema, the abnormal or excessive retention of fluid at a site in the body, can produce damaging stress on the body and inhibit proper functioning of organs. Edema inhibits blood flow in tissue, raises systemic blood pressure and otherwise impairs healthy body function. It is often associated with low blood flow and its attendant problems and can affect any location or organ of the body. When excessive fluid collects in tissue there is a need to mitigate the condition to avoid related adverse physiological effects and as an aid to treatment of underlying conditions.

Edema produces swelling which can result in a constriction of blood flow to an affected area. This can place stress on the heart, kidneys, brain, muscle tissue and other organs. Causes of edema include trauma, burns, hypersensitive reactions, thrombophlebitis and disease. Edema can even result from malnutrition, obesity and lack of exercise. In the heart, edema can produce heart failure. Cardiac edema increases the volume of the heart wall; the wall thickens and reduces the volume of the chambers of the heart. Cardiac output is reduced and the workload of the heart is increased. In muscle tissue edema can produce compartment syndrome. Injury can cause a volume of tissue to retain excess fluid and swell. The volume of the swelling tissue is constrained by surrounding tissue so that blood supply to the tissue is restricted.

Water content of tissue can change from time-to-time, and sometimes rapidly so there is a need for an edema monitor which can detect tissue water content in any tissue or organ of the body and monitor it continuously.

Head trauma often results in brain edema and a need to monitor. Serious head injury is almost always associated with excessive fluid retention in brain tissue and brain swelling. As the brain swells the increase in tissue volume is confined by the rigid cranial cavity. The resulting pressure increase restricts blood supply and, if not relieved, produces brain damage.

It has been reported that over 270,000 people in the US are hospitalized for traumatic brain injury each year from vehicular crashes, falls, assaults and other reasons and of these 50,000 to 100,000 deaths occur per year, representing approximately one third of all traumatic brain injuries. In addition, brain injury occurs as a result of subarachnoid hemorrhage and intra-cerebral hemorrhage, afflicting approximately 100,000 people each year in the US. Costs associated with treatment, hospitalization and rehabilitation after traumatic brain injury is estimated at $48.3 billion annually.

Brain trauma induces primary and secondary injury processes. Secondary injury can be due to ischemia and can initiate of a cascade of pathophysiological and biochemical events leading to necrosis, apoptosis and inflammation. Subarachnoid, intraventricular or intraparenchymal hemorrhage can result in focal or diffuse cerebral edema.

Brain edema also occurs to varying degrees in acute traumatic brain injury, hyponatremia (e.g., liver failure), cardiac arrest, and stroke. Brain edema could also occur in chronic conditions such as tumor progression and secondary to cerebral ischemia or hypertensive encephalopathy. The resulting effects of cerebral edema can be deadly. Increased edema volume in the confined space of the cranium increases intracranial pressure which can lead to complete cessation of the cerebral circulation and brain death. The brain can suffer irreversible damage after seven to eight minutes of oxygen deprivation. It has little energy reserves and is highly sensitive to decreased perfusion or oxygen levels.

Since the brain is in a closed space (the cranium), cerebral edema (swelling) causes the intracranial pressure (ICP) to increase. The pressure that drives blood through the capillary beds or the cerebral perfusion pressure (CPP) is the mean arterial blood pressure (MAP) minus the ICP:

$$CPP=MAP-ICP \qquad (1)$$

Assuming mean arterial blood pressure (MAP) stays relatively constant, an increase in edema and intracranial pressure (ICP) will consequently cause a decrease in cerebral perfusion pressure (CPP) and cerebral blood flow (CBF). This will reduce the oxygen supply to the brain, increase anaerobic metabolism, deplete the glucose supply, release hydrogen ions, and induce intracellular lactic acidosis and brain edema. This leads to a vicious circle of decreasing cerebral blood flow and increasing edema. Ischemia with CBF<18 ml/100 g/min in the first six hours after the primary injury correlates with poor patient outcome. Of note, approximately 80% of severe head injury deaths are caused by secondary injuries. Therefore the detection and reversal of secondary brain ischemic injury is the goal of traumatic brain injury treatment strategies after the immediate effects of the primary injury have been addressed.

Currently, intracranial pressure is among the most commonly monitored variables in cases of head injury. According to the Brain Trauma Foundation, intracranial pressure is monitored in about 78% of neurosurgical intensive care units. Intracranial pressure can be monitored through a ventriculostomy or with an intraparenchymal catheter placed through a burr hole and secured via a bolt. Intracranial pressure (ICP) is used with mean arterial pressure (MAP) to obtain cerebral perfusion pressure (CPP) which represents the pressure gradient across the cerebrovascular bed (see Equation 1).

Numerous techniques have been proposed that attempt to determine if the brain is getting adequate oxygen and a few techniques have attempted to predict the evolving status of cerebral tissue including the presence and magnitude of edema. CT can be used to qualitatively assess water content, but it is not routinely performed at the bedside. MR techniques have been used to quantitatively assess water content, but MR also does not lend itself to routine, bedside monitoring.

Intracranial pressure remains the standard for neuromonitoring of brain injured patients. Intracranial volume is made up of three components, cerebral blood volume (CBV), cerebrospinal fluid (CSF) volume and brain tissue volume which is subject to brain edema volume. An increase in intracranial pressure is the direct and eventual result of a combination of cerebral edema volume and increased cerebral blood volume (CBV). By the time intracranial pressure starts to increase to pathological levels, brain edema and cerebral blood volume have already progressed to the point where all the available space in the cranium is occupied. As a result, therapy has to rapidly follow any substantial increase in intracranial pressure, making the patient care regimen, very reactive.

Treatment strategies in the management of high intracranial pressure, usually a Consequence of brain edema and increased cerebral blood volume, are guided by two primary concepts. One approach is to target cerebral perfusion pressure where it is progressively increased in order to maintain cerebral blood flow and thereby increase oxygen delivery. However, if an increase in cerebral perfusion pressure elicits an increase in intracranial pressure as may occur where there is loss of autoregulation, then increasing cerebral perfusion pressure is not an option as intracranial pressure will also increase and brain herniation may occur. Thus, alternate interventions sometimes used involve the use of drugs such as beta adrenergic blockers, alpha one agonists, barbiturates and sedatives to target the reduction of intracranial pressure rather than increasing cerebral perfusion pressure.

The most commonly used methods to decrease and maintain intracranial pressure and ameliorate the effect of edema is to drain cerebrospinal fluid (CSF), which leaves more cranial space to be occupied by swelling brain tissue, and to administer osmotic diuretics, such as mannitol or hypertonic saline, which remove water from the tissue and counteract the effects of edema. Cranial perfusion pressure can be increased by increasing mean arterial blood pressure using vasopressors. The use of hypertensive agents, however, remains very controversial. High cranial perfusion pressure may also increase intracranial pressure through edema formation by increased transcapillary filtration. Also vasoconstrictors, which increase mean arterial blood pressure, may decrease cerebral blood flow due to the increased vascular resistance.

In general, the effect of therapies on edema, intracranial pressure and cerebral blood flow may vary from patient to patient. Intracranial pressure is routinely and continuously monitored in patients with severe head injury, cerebral blood flow is increasingly being used in the clinic, but there is no available device to monitor cerebral edema in real time and at the bedside. There is a need for quantitative continuous or near-continuous monitoring. There is a need to improve that capability, quantify brain water content and further to separate intra vascular water from extra vascular water.

SUMMARY OF THE INVENTION

It is an object of this invention to provide a real-time, bedside monitor that can quantify edema.

It is an object of this invention to provide an edema monitor that separates in a volume of tissue the contributions to the tissue total water of intravascular water and extravascular water.

Real-time and continuous edema monitoring can help:
Rapidly and accurately target therapy;
Provide an early warning indicator for ischemic events;
Provide prognostic information;
Customize therapy for individual patients;
Provide a real-time monitor of the effect of therapy on tissue water content; and
Elucidate neurophysiology of brain-injured patients.

In patients with severe head injury intracranial pressure is routinely and continuously monitored. However, the neurocritical care community has realized that intracranial pressure alone does not provide enough information to adequately monitor and treat the brain, the most complex organ in the human body.

Accordingly, it is an object of this invention to provide a system for monitoring brain-injured patients by supplementing intracranial pressure with edema.

It is also an object to provide a monitoring strategy that can conveniently be used in conjunction with intracranial pressure monitoring, in real time and track and follow the trajectory of brain injury as well as the efficacy of therapies. The ability to quantitatively track the response of therapeutic interventions on cerebral edema is of tremendous help in the clinical management of high intracranial pressure in patients after brain injury.

A preferred embodiment of this invention addresses the quantification of cerebral edema. Cerebral edema is classified as follows:
Cytotoxic: increased water content inside cells and is due to failure of ion pumps;
Vasogenic: damage to blood-brain barrier results in fluid shift from Mott- to extra-vascular space;
Interstitial: increased transependymal flow from the intraventricular compartment to the brain parenchyma (e.g., obstructive hydrocephalus); and
Osmotic: decreased blood plasma osmolality relative to the cerebral tissue (caused by excessive water intake, among others) causes vascular water to cross the blood-brain barrier.

In the present invention, the monitoring of water content (edema) in live tissue is provided by detecting the thermal response of the subject tissue to the application of thermal energy and computing water content as a function of the thermal response and thermal energy or power used. Certain thermal properties of tissue vary as a function of tissue water content. For example, thermal diffusivity and thermal conductivity of the tissue increase as the water content of the tissue increases. Accordingly, the thermal response to the introduction of heat in a selected tissue sample or organ is a function of these properties.

A thermal probe incorporates an embedded thermistor that thermally communicates with tissue in contact with it and electrically communicates with a data processor. In a minimally invasive probe, a distal thermistor is embedded in the tip of a narrow gage catheter (1-mm diameter). The catheter is inserted into tissue at a site to be examined and effects thermal contact with surrounding tissue. The thermistor, adapted for thermal contact with the tissue, is heated to a small increment above the tissue temperature baseline. (For example the temperature of the thermistor surface may be elevated to a predetermined temperature approximately 2.degree. C. above the tissue temperature baseline.) A second or proximal thermistor may be embedded in the probe for monitoring tissue baseline temperature and compensating for baseline temperature fluctuations. The distal thermistor is heated at intervals by a power source within a control circuit. The power used to elevate the temperature in an interval is indicative of a value of the selected thermal characteristic, for example, thermal conductivity and/or thermal diffusivity, in tissue at the location of the thermistor. The sensed temperature results in a signal from the power source functionally related to the thermal response in the tissue to the application of heat, which signal is used to calculate a value indicative of tissue water content. The following example is based on thermal conductivity.

When the thermistor is in thermal contact with live tissue at a site where water content is to be assessed, the power dissipated by the heated thermistor (typically within the range of 0.005-0.01 W) provides a measure of the ability of the tissue to carry heat by both conduction in the tissue and convection due to tissue blood flow. In operation, the thermistor is energized and a thermal field propagates into tissue contacting and surrounding the thermistor. The initial propagation of the field is due substantially to inherent tissue conductivity (thermal conductance). Subsequent propagation of the field is affected more by tissue convection (blood flow or perfusion). A monitor or data processor controls the probe, records the data and distinguishes between the effect of the inherent thermal conductivity characteristic of the tissue and convective heat transfer due to tissue blood flow. The inherent or intrinsic thermal conductivity of the tissue at the site of the thermistor is determined from the initial rate of propagation of the thermal field in the tissue, separated from the effects of convective heat transfer.

A data processing technique by which the thermal conductive and convective effects of the heated thermistor are distinguished and separated will now be discussed. Measurements are made under effectively transient conditions, i.e., at times which are short relative to the time required for the system to reach steady state. Accordingly, the temperature change produced in the tissue is permitted to vary in any arbitrarily selected manner with time. The power required to heat the tissue and the resulting temperature change are recorded. An intrinsic thermal conductivity value is calculated using data obtained at an initial time period. The conductivity value is used to assess the fluid content (or edema) of tissue at the site of the probe. The water content of the tissue is computed as a function of the intrinsic thermal conductivity of the tissue and data derived by using a model of the relationship of intrinsic tissue conductivity values to tissue water content values.

As is often the case in monitoring procedures, there is some margin of error that must be held within a range deemed appropriate for acceptable or optimum operation. When direct computation of conductivity (or other thermal property) does not lead to an acceptably accurate calculation of water content, an iterative process may be used to optimize the accuracy of the water content calculation. For example, computation can be based on a thermal model requiring a series of heating cycles with measurements at two or more selected times within each cycle. These measurements occur during a temperature change cycle in which the temperature of tissue at the selected site is raised from a first unperturbed value to a second value and relaxed back to an unperturbed value. A thermal model and related mathematical equations are described in U.S. Pat. No. 4,852,027 to Bowman et al, incorporated herein by reference. When data used to assess the thermal conductivity of tissue includes measurements made at least two selected time periods in an overall temperature changing cycle, data processing occurs in an interactive or iterative operation so as to converge relatively rapidly to a final solution for conductivity of tissue at the site of the probe. In one embodiment, the thermistor is energized to heat the tissue at the selected site from an unperturbed temperature value to a second higher temperature value and then permitted to decay, i.e. to cool, to an unperturbed value. Power is applied to energize the thermistor in any appropriate manner that produces an arbitrarily selected change as a function of time in the volume mean temperature of the tissue surrounding the thermistor. Measurements are made in at least two selected time periods during the heating and cooling cycle. The effects of the flow in the tissue (perfusion) on the measurements involved are least (substantially negligible) during the initial stage of the heating cycle and greater during the later portion of the cycle. Particularly, the effects of flow are greater during the cooling portion of the cycle than during the heating portion.

In the iterative computation, the temperature of the thermistor is caused to rise to initiate each heating cycle and relax at the end of each cycle. An initial determination of a value for intrinsic thermal conductivity (or thermal diffusivity), is calculated during a first time period in the initial and each subsequent heating cycle. This first time period calculation is made at the initial stage of each heating cycle. A calculation of the convective heat transfer effect in the tissue due to perfusion of the tissue is separately calculated at a second time period, later in the heating cycle, using the conductivity value obtained in the initial time period and perfusion data obtained at the second time period, the effects of convective heat transfer during the second time period being greater than the convective heat transfer effects during the first time period. The perfusion value obtained at the second time period of a particular cycle is used to recompute a second, more accurate value of thermal conductivity in the first time period of a subsequent cycle. The process can be repeated as many times as necessary. In each calculation of perfusion the value of conductivity obtained in the prior calculation is used. Similarly, in each successive computation of thermal conductivity the prior value of perfusion is used. The iterative process will lead to convergence wherein the same value of thermal conductivity is obtained in successive calculations. This value of conductivity can be used to compute the fluid content of tissue at the location of the probe.

The calculation of edema in the above described embodiment thus takes into account the effective thermal conductivity of the subject tissue, that being the convective heat transfer effect produced by tissue perfusion plus the intrinsic thermal conduction of the tissue, and separates the convective heat transfer effect (perfusion) from the intrinsic thermal conductivity. (Similarly, effective thermal diffusivity is the intrinsic thermal diffusivity of the tissue plus the perfusion related diffusivity effects.)

The minimally invasive thermal probe used in conjunction with the monitor is typically placed through a burr hole in one of the frontal lobes (either with a cranial bolt or tunneled) and the catheter tip is positioned about 2.5 cm below the dura in the white matter. The thermistor at the catheter tip is heated to a small increment (~2° C.) above the tissue baseline temperature. The temperature rise and the power required to maintain a constant thermistor temperature are a function of the heat transported from the thermistor to the tissue via thermal conduction and thermal convection (capillary blood flow). The bioheat equation is used to model the thermal physics in the tissue:

$$\rho c \frac{\partial T}{\partial t} = K \nabla^2 T - \omega \rho_b c_b T \tag{2}$$

where $\rho$ is the tissue density, c is the tissue specific heat, T is the temperature rise in tissue, K is the tissue thermal conductivity, $\omega$ is the tissue perfusion (blood flow), $\rho_b$ is the blood density and $c_b$ is the blood specific heat.

An algorithm in the monitor software separates the conduction and convective components (the right side of Equation (2)) to quantify perfusion in absolute, physiologic units (ml/min-100 g of tissue) by solving the following equations.

$$P = \frac{4\pi a K \Delta T}{\frac{K}{5k_b} + \frac{1}{1+\lambda a}} \left[ 1 + \frac{\frac{a}{\sqrt{\pi \alpha_m}} f(t)}{\frac{K}{5k_b} + 1 + \lambda a} \right]$$

-continued $$f(t) = \frac{1}{\sqrt{t}}\left[e^{-\lambda^2 \alpha_m t} - \sqrt{\pi \lambda^2 \alpha_m t}\, \text{erfc}(\sqrt{\lambda^2 \alpha_m t})\right]$$

$$\lambda = \sqrt{\frac{\omega c_{bl} \rho_{bl}}{K}}$$

where P is the power dissipated in the thermistor, a is the radius of the thermistor, K is tissue thermal conductivity, $\Delta T$ is the temperature rise in the thermistor, $k_b$ is the thermal conductivity of the thermistor, $\alpha_m$ is the thermal diffusivity of the tissue, t is time, $\omega$ is tissue perfusion, $c_{bl}$ is the blood specific heat and $\rho_{bl}$ is the blood density.

Tissue thermal conductivity (K), computed as an intermediate step in the algorithm to quantify blood flow, is a function of the total water content of the tissue that surrounds that thermistor. Macroscopically, tissue consists of protein, fat and water. The thermal conductivity of tissue is a function of both the mass fractions of these constituents and the thermal conductivity of each constituent. The thermal conductivity of water (at 37° C.) is 6.23 mw/cm-K and the thermal conductivity of protein and fat is each approximately 2 mw/cm-K. The total water content of tissue can be computed from the measurement of K. Total tissue water content includes intravascular and extravascular water. (Extravascular water includes intracellular and extracellular water.) An increase in extravascular water that is not already contained in the cerebrospinal fluid (CSF) is primarily responsible for edema.

Methods and apparatus for determining properties of a medium by causing a thermal change in the medium and then calculating it's properties based on the medium's response to the thermal change are described in detail in the following patents which are incorporated herein by reference: U.S. Pat. No. 4,059,982 to H. F. Bowman issued Nov. 29, 1977; U.S. Pat. No. 4,852,027 to H. F. Bowman and W. H. Newman issued Jul. 25, 1989; U.S. Pat. No. 5,035,514 to W. H. Newman issued Jul. 30, 1991; U.S. Pat. No. 6,488,677 to H. F. Bowman and G. T. Martin issued Dec. 3, 2002, U.S. Pat. No. 7,758,511 to a T. Martin & H. F. Bowman issued Jul. 20, 2010 and U.S. Pat. No. 8,454,525 to G. T. Martin & H. F. Bowman issued Jun. 4, 2013.

The edema monitor of this invention uses patient specific measurements of tissue conductivity (k), tissue perfusion ($\omega$), tissue total water (TW) and an empirically developed perfusion coefficient of thermal conductivity ($m_\omega$) to isolate tissue intravascular water (TIW) and tissue extravascular water (TEW) components of tissue total water (TW). Total tissue water can be expressed as:

$$TW = TIW + TEW$$

Where:

$$TIW = 100\left(\frac{m_\omega \omega}{k_{H2O} - k_t}\right),$$

and $$TEW = 100\left(\frac{k_m - k_t - m_\omega \omega}{k_{H2O} - k_t}\right)$$

Substituting expressions for TIW and TEW yields:

$$TW = 100\left(\frac{m_\omega \omega}{k_{H2O} - k_t}\right) + 100\left(\frac{k_m - k_t - m_\omega \omega}{k_{H2O} - k_t}\right)$$

where TW is total tissue water, TIW is tissue intravascular water, TEW is tissue extravascular water, $m_\omega$ is the perfusion coefficient of thermal conductivity, $\omega$ is tissue perfusion, $k_m$ is measured tissue thermal conductivity, $k_t$ is the thermal conductivity of dry brain tissue and $k_{H2O}$ is the conductivity of water.

It is an excess in the extravascular water (TEW) component that primarily gives rise to edema.

The empirically developed perfusion coefficient of thermal conductivity ($m_\omega$) enables a calculation to be made of tissue intravascular water (TIW). The calculated value for tissue intravascular water (TIW) is subtracted from the measured value of total water (TW) to obtain a value for tissue extravascular water (TEW). A clinically accepted value for normal tissue water content is subtracted from the value obtained for tissue extravascular water (TEW) to obtain a value for edema.

The thermal conductivity of water and of tissue is temperature dependent. The temperature coefficient of thermal conductivity, experimentally identified, is incorporated in the tissue extravascular model.

In a study using the dry weight of tissue after biopsy, the water content in the white matter of comatose patients with cerebral edema was found to be 80.94%±2.5% and 75.28%±2.3% after the administration of mannitol (Nath, F., & Galbraith, S., "The Effect of Mannitol on Cerebral White Matter Water Content", *Journal of Neurosurgery*, 65(1), 41-43, 1986.). Thus a system that monitors cerebral edema and resolves changes to about 2% or better will provide useful information that correlates with clinical interventions.

The Bowman Perfusion Monitor sold by Hemedex, Inc. of Cambridge, Mass., USA, and described in the above mentioned patents can be used in connection with this invention to compute conductivity (k) and perfusion ($\omega$) as steps in the determination of edema. Conductivity is computed periodically, every time the monitor automatically performs an in situ recalibration to assess tissue properties, for example, about every 15-30 minutes. Conductivity values are computed to an accuracy better than 1%.

Thermal conductivity based tissue water content measurements establish a new clinical technique. The system separates the intravascular and extravascular contributions to tissue thermal conductivity, K, thus permitting a high degree of accuracy in the quantification of cerebral edema. Cerebral edema can be quantified and monitored in real time at the bedside. The system provides an early warning for impending and pathological increases in intracranial pressure and decreases in cerebral blood flow associated with edema. This monitoring system can be used to evaluate and select treatment modalities.

DESCRIPTION OF THE PREFERRED EMBODIMENTS

Heat transfer in tissue consists of a thermally conductive component and a thermally convective component resulting from perfusion. These components must be separated mathematically to realize the most accurate and reproducible measurement of thermal conductivity and perfusion in absolute physiologic values. The present system uses a series of algorithms that permit reliable quantification of tissue perfusion by accurately determining the conductive properties of the tissue from the initial rate of propagation of the thermal field and separating this component from the total heat transfer to determine the thermal convection component (Valvano, J T Allen, and H F Bowman, "The Simultaneous Measurement of Thermal Conductivity, Thermal Diffusivity, and Perfusion in Small Volumes of Tissue", *ASME J. of Biomech. Eng.*, 106:192-197, August 1984.)

Measured brain tissue thermal conductivity ($k_m$), an intrinsic property, is equivalent to the sum of the thermal conductivities of the brain constituents (i.e., dry brain tissue ($k_{bt}$=1.95 mW/cm-° K) and water ($k_{H2O}$=6.23 mW/cm-° K)) in their volumetric proportion. If total brain water (BW) is the percent of the brain that is water, then:

$$k_m = \left(\frac{BW}{100}\right)k_{H2O} + \left(1 - \frac{BW}{100}\right)k_{bt} \qquad (3)$$

Rearranging (3) to calculate total brain water (in percent), yields:

$$BW = 100\left(\frac{k_m - k_{bt}}{k_{H2O} - k_{bt}}\right) \qquad (4)$$

Total brain water (BW) consists of brain intravascular water (BIW) associated with perfusion and brain extravascular water (BEW), which in excess is edema. That is:

$$BW = BIW + BEW \qquad (5)$$

Brain intravascular water is a function of perfusion; increasing perfusion increases vascular volume and total brain water, and therefore the measured thermal conductivity. Consequently, $k_m$ is parsed into two components, one linearly proportional to intravascular flow (i.e.: $m_\omega \omega$) and the remaining portion (i.e.: $k_m - m_\omega \omega$) associated with extravascular water. That is, $$k_m = f(\omega) + (k_m - f(\omega))$$

where $\omega$ is perfusion. Here we employ a linear model (as supported by the data shown in FIGS. 2(*a*) and 2(*b*))) in which the intravascular component is linearly proportional to flow (i.e.: $f(\omega) = m_\omega \omega$). Thus, the partitioning of $k_m$ as shown in FIGS. 1A and 1B is expressed as:

$$k_m = (m_\omega \omega) + (k_m - m_\omega \omega) \qquad (6)$$

where $m_\omega$ is an empirically derived perfusion coefficient of thermal conductivity.

Figure 1A:
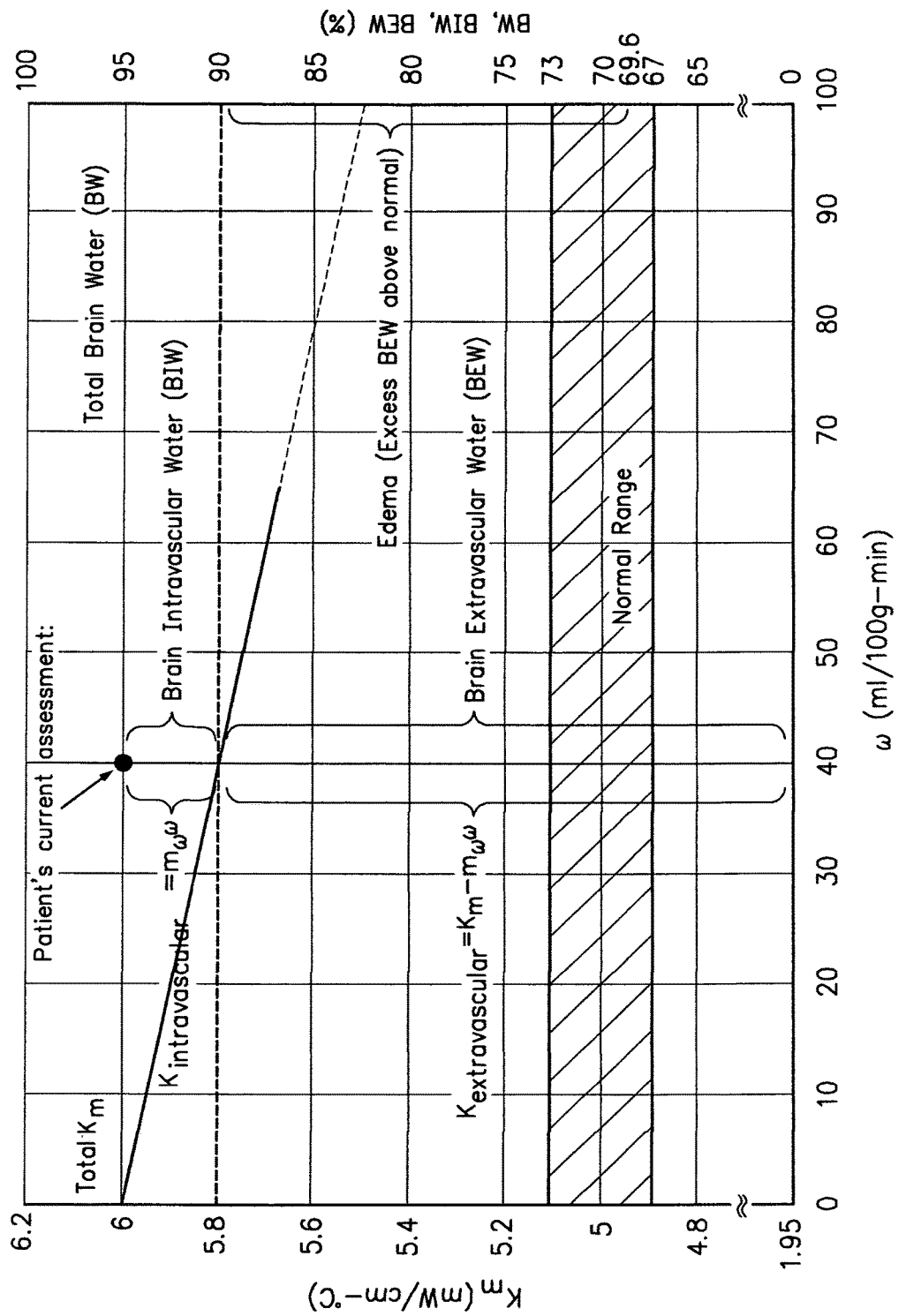
FIG. 1A is a plot showing the relationship of brain intravascular water and brain extravascular water.
Figure 1B:
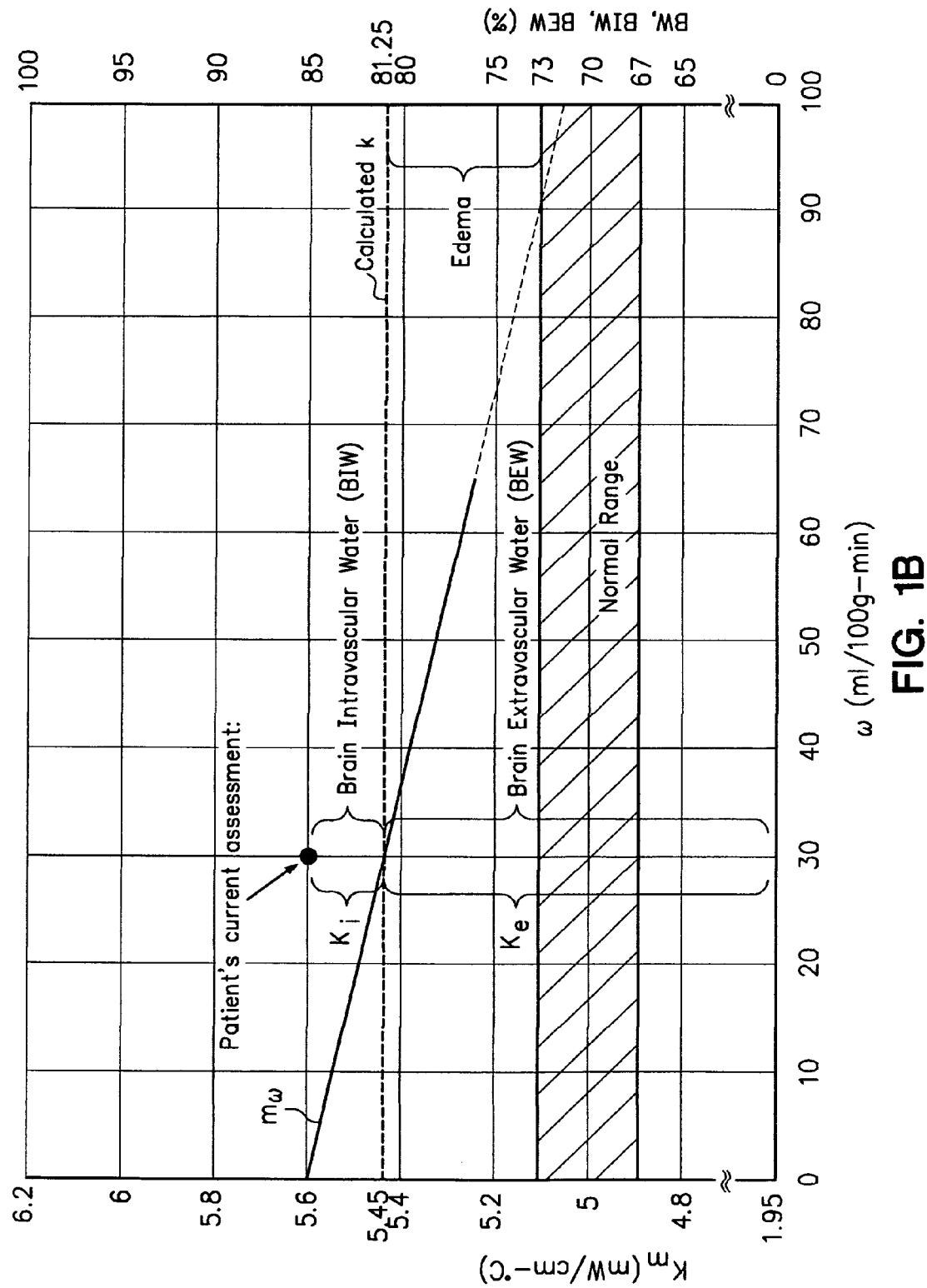
FIG. 1B is a second plot showing the relationship of brain intravascular water and brain extravascular water.

FIGS. 1A and 1B are for illustrative purposes. These figures illustrate the calculation of edema from measured thermal conductivity and perfusion values and the perfusion coefficient of thermal conductivity $m_\omega$. The specific values of conductivity and tissue water content shown along the Y axes are for illustration purposes and are not necessarily precise. For example, the value 1.95 mw/cm-° C. represents the thermal conductivity of dry brain tissue and the value 6.2 mw/cm-° C. represents the thermal conductivity of pure water at 37° C. (The vertical scale extends from 0% water to 100% water as seen on the right vertical axis representing percent water content.) While 1.95 mw/cm-° C. is a published value for the thermal conductivity of dry brain tissue, the true value may be considered to be slight variants up or down of this value. Also, a more precise value for the thermal conductivity of pure water at 37° C. is 6.23 mw/cm-° C. Further, by way of explanation, perfusion is shown in units of 0 ml/100 g-min to 100 ml/100 g-min, that is from a no flow condition to a condition well above normal levels of perfusion in brain white matter. A perfusion range of 20 ml/100 g-min to 40 ml/100 g-min is illustrative of the normal range of white matter perfusion.

In the example shown in FIG. 1A, the measured $k_m$ and $\omega$ are shown, respectively, as 6 mw/cm-° C. and 40 ml/100 g-min. The perfusion coefficient of thermal conductivity $m_\omega$ is shown in FIG. 1A as the diagonal line extending from the measured value of $k_m$ on the Y axis and having a negative slope of 0.005, passing through the line indicating measured $\omega$. (Determination of the slope is described hereafter in connection with FIGS. 2A and 2B.) The intercept between the line representing the perfusion coefficient of thermal conductivity and the line representing measured a) defines the separation of brain intravascular water and brain extravascular water.

In FIG. 1A a plot of thermal conductivity ($k_m$) and total brain water (BW) versus perfusion ($\omega$) illustrates the two additive contributors to thermal conductivity and their associated contributions to total brain water. Edema can be considered the excess extravascular water in the tissue above a normal value of extravascular water (69.6%±1%) or above a value within a range of values considered normal (67-73%). The normal value of tissue water can be modeled by a chosen value supplied by a memory chip or by an expression that captures a range of values.

Thermal conductivity is an intrinsic property of the material (e.g.: tissue or brain tissue) and is proportional to total brain water (BW). Total brain water (BW) is the sum of brain intravascular water (BIW) and brain extravascular water (BEW). Brain intravascular water is proportional to perfusion ($\omega$). Brain extravascular water is obtained by subtracting brain intravascular water from total brain water. Brain extravascular water above normal levels or values is considered edema. (Brain extravascular water includes intracellular water and extracellular water.)

Figure 2A:
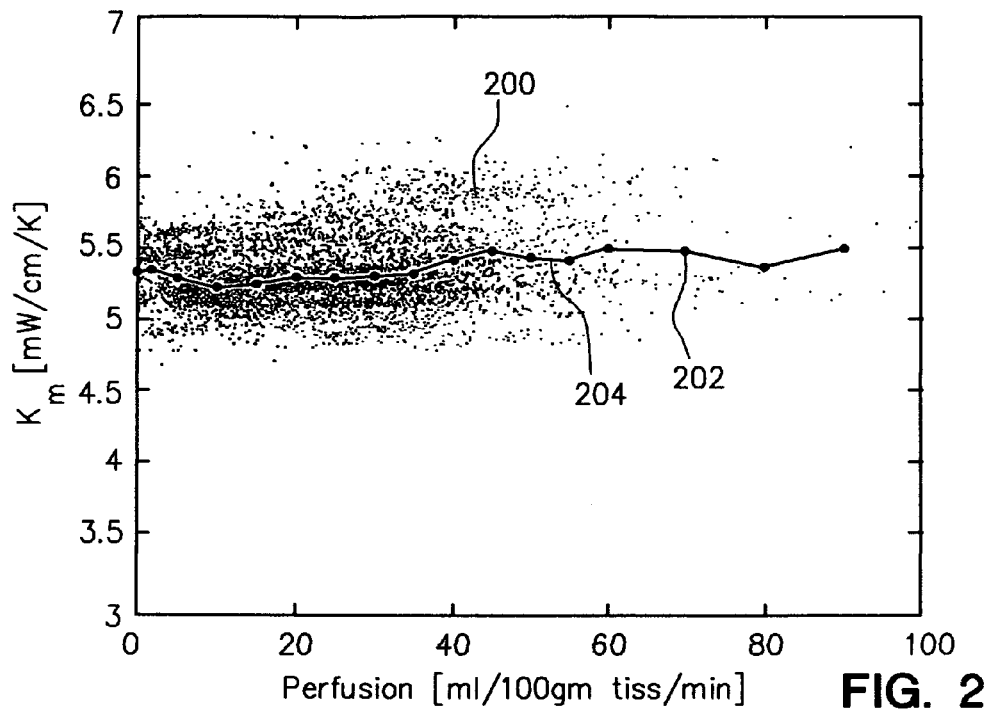
FIGS. 2A and 2B are plots relating to the derivation of a perfusion coefficient of thermal conductivity.
Figure 2B:
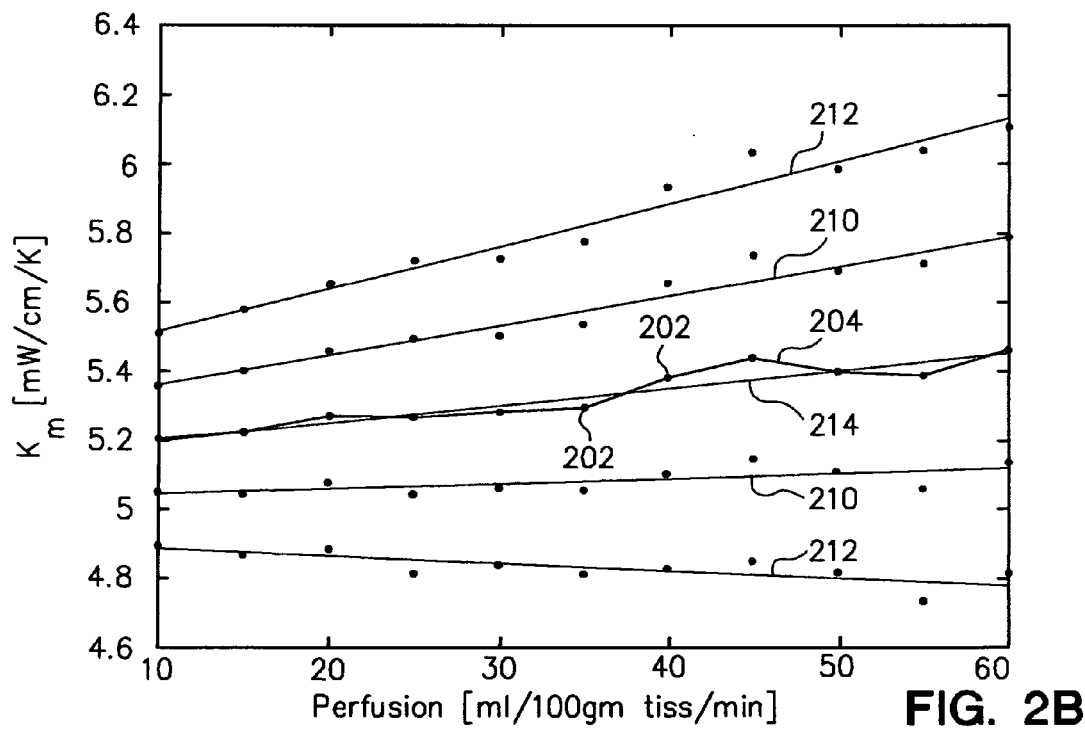

FIGS. 2A and 2B graph an empirical derivation and modeling of the perfusion coefficient of thermal conductivity ($m_\omega$) (i.e., the increase in thermal conductivity per unit of perfusion). In FIG. 2A more than 6500 raw clinical data points (200) relating brain thermal conductivity to perfusion level are plotted. The large dataset (>6500 measurements) from a variety of clinical recordings (data points 200 in FIG. 2A) were grouped into bins of perfusion (in increments of 5 ml/100 g-min); the mean thermal conductivity taken for each bin was plotted (points 202 in FIGS. 2A and 2B). This data suggests a linear association between conductivity and perfusion in the observed range of flow.

Since little data was available at high perfusion levels (>60 ml/100 g-min), that data is excluded from the analysis to determine $m_\omega$. For data at very low perfusion levels (<10 ml/100 gm/min), the increased conductivity is believed to be due to edema (and not intravascular fluid) in swellinginduced, compromised-flow states; thus it does not represent normal physiology and is also excluded from the analysis to determine $m_\omega$.

In FIGS. 2A and 2B the line 204 connects the mean thermal conductivity points 202 and suggests a linear fit. In FIG. 2B the linear fit 214 between conductivity and perfusion ($k_m$=5.140+0.005$\omega$, $R_{sq}$=0.07, p<0.001) is shown in the range of flow (10-60 ml/100 g-min). Also shown in FIG. 2B are the mean values of conductivity 202 for each perfusion bin, the first standard deviation 210 and the second standard deviation 212.

In FIG. 2B, the line 204 connecting mean values (202), the linear fit (214) and standard deviations ±1 (210) and ±2 (212) of the data are plotted for the values in the 10-60 ml/100 g-min range ($k_m$=5.140+0.005$\omega$; $R_{wq}$=0.07, p<0.001). The slope is found to be 0.005. Consequently, from the empirical the data, the perfusion coefficient of thermal conductivity ($m_\omega$) is determined to be 0.005, the slope of linear fit 214. The linear fit 214 between conductivity and perfusion models the perfusion coefficient of conductivity ($m_\omega$) which model appears in FIGS. 1A and 1B as the sloped line.

Substituting the perfusion-specific expression for thermal conductivity (6) into the equation for total brain water (5) yields BIW and BEW as the left and right terms in the resultant expression:

$$BW = 100\left(\frac{m_\omega \omega}{k_{H2O} - k_{bt}}\right) + 100\left(\frac{k_m - k_{bt} - m_\omega \omega}{k_{H2O} - k_{bt}}\right) \quad (7)$$

That is, $$BIW = 100\left(\frac{m_\omega \omega}{k_{H2O} - k_{bt}}\right), \quad (8)$$

and $$BEW = 100\left(\frac{k_m - k_{bt} - m_\omega \omega}{k_{H2O} - k_{bt}}\right) \quad (9)$$

where BW is total tissue water, BIW is tissue intravascular water, BEW is tissue extravascular water, $m_\omega$ is the perfusion coefficient of thermal conductivity, $\omega$ is tissue perfusion, $k_m$ is measured tissue thermal conductivity, $k_{bt}$ is the thermal conductivity of dry brain tissue and $k_{H2O}$ is the conductivity of water.

Figure 3:
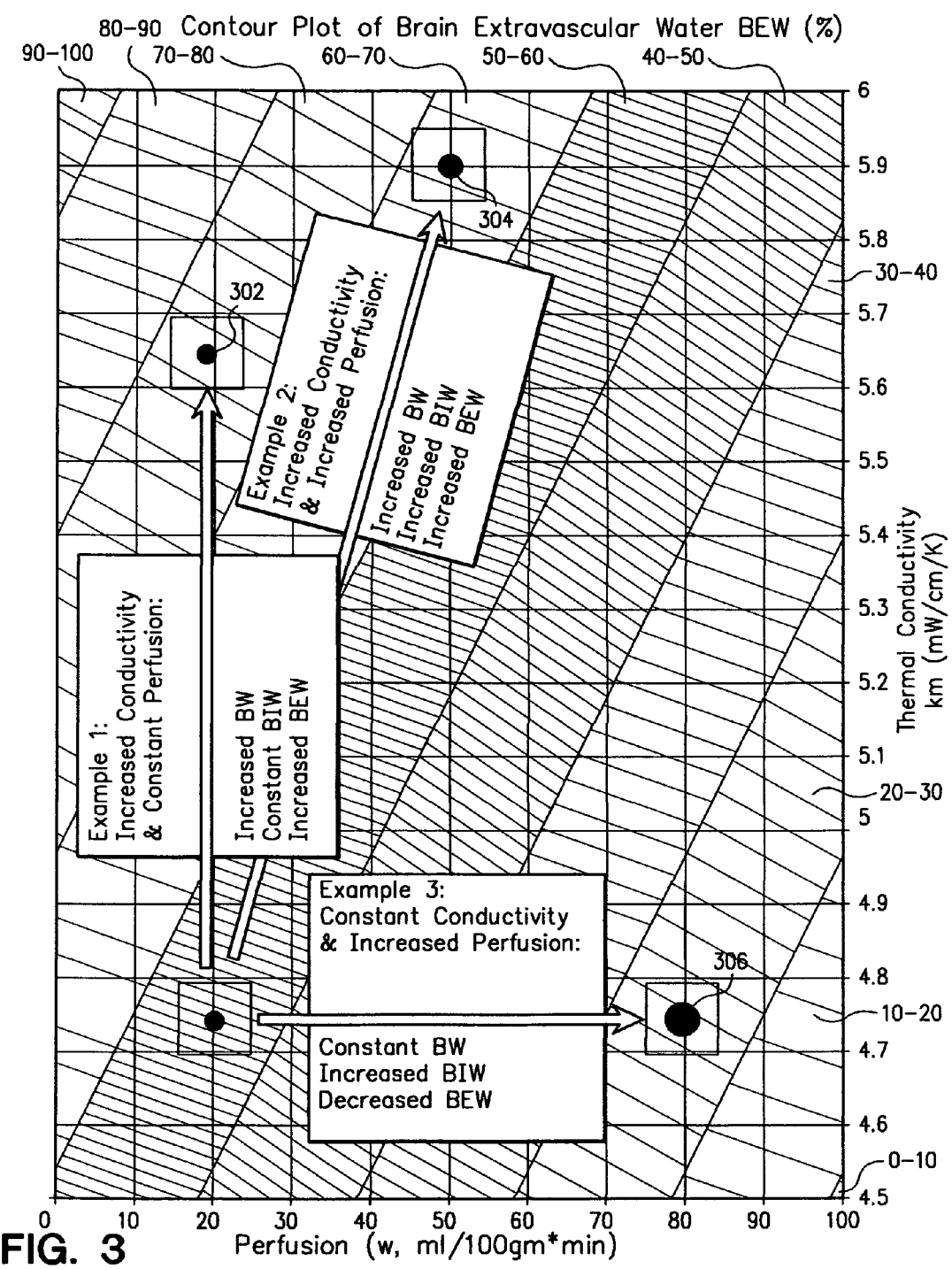
FIG. 3 is a contour plot of brain extravascular water.

The plot of brain extravascular water in FIG. 3 illustrates how independent changes in thermal conductivity and perfusion impact brain extravascular water, the clinically relevant factor for monitoring edema. FIG. 3 is a Contour Plot of Brain Extravascular Water (leftward diagonal bands being associated with higher water content) as a function of thermal conductivity ($k_m$) and perfusion ($\omega$). Relative changes in Brain Intravascular Water (BIW) are indicated by the size of the circles 302, 304 and 306 (which is not drawn to scale.) Examples 1-3 demonstrate changes in brain intravascular water (BM) and brain extravascular water (BEW) for three clinical scenarios. (Perfusion and thermal conductivity values are approximate; in each example the beginning perfusion value is 20 ml/100 gm-min and beginning thermal conductivity is 4.74 mw/cm-° K.) (Example 1) Conductivity increasing to 5.64 mw/cm-° K with constant perfusion (circle 302) is associated with increased BW, constant BIW and increased BEW. (Example 2) Conductivity increasing to 5.90 mw/cm-° K and perfusion increasing to 50 ml/100 gm-min (circle 304) is associated with increased BW, increased BIW and increased BEW. (Example 3) Constant conductivity with an increase in perfusion to 80 ml/100 gm-min (circle 306) is associated with constant BW, increased BIW and decreased BEW.

Figure 4:
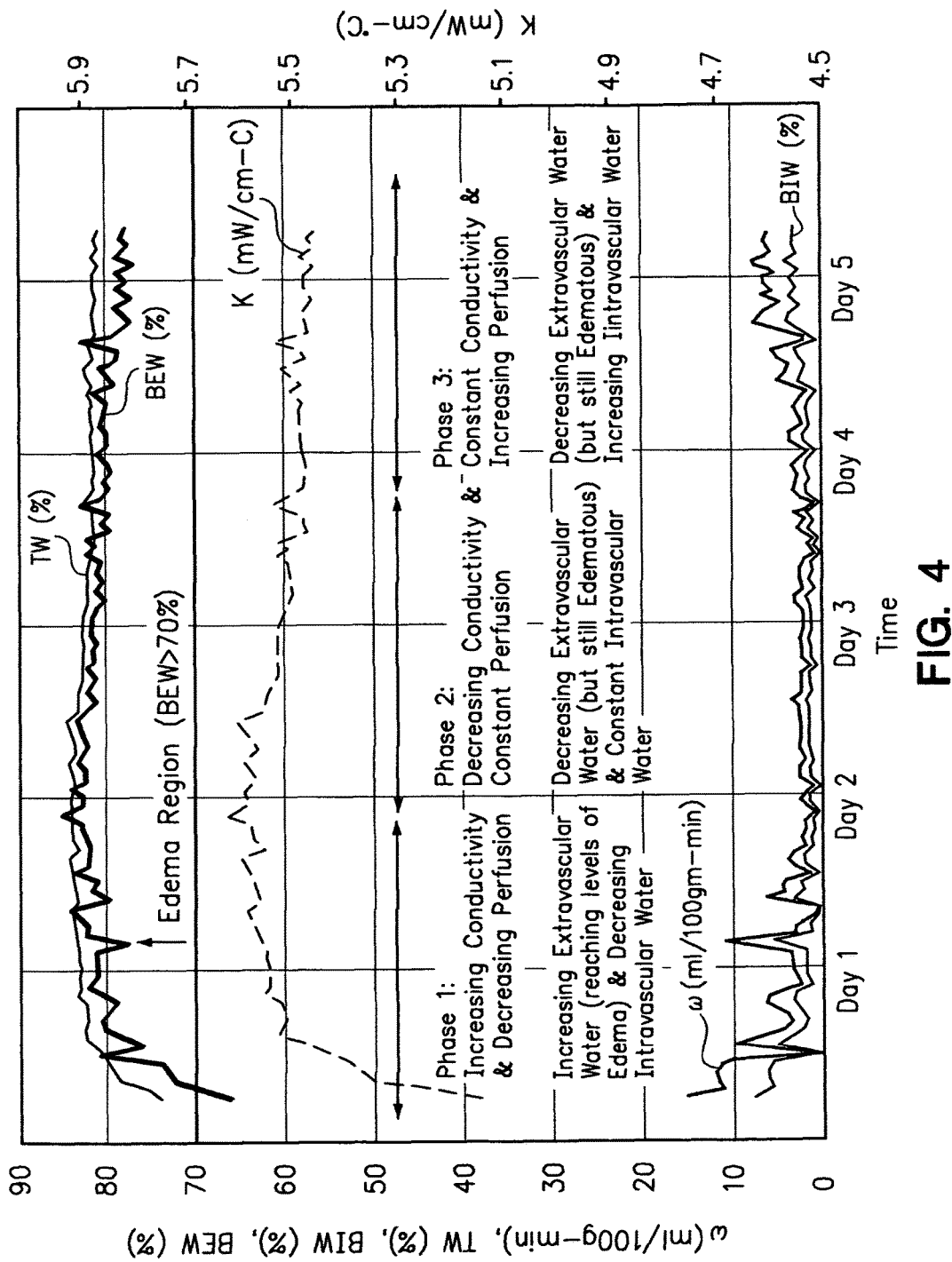
FIG. 4 shows three phases of edema development.

A plot to investigate and quantify edema of a typical patient with very low perfusion and concomitant edema is shown in FIG. 4. Note the inverted relationship between conductivity (K) and perfusion ($\omega$), demonstrating the pathophysiology associated with the onset and partial resolution of edema. (Normally, conductivity increases with perfusion as demonstrated in FIG. 1A.) Given that normal white matter can be considered to contain 69.6±1% extravascular water (illustrated as 70% in FIG. 4), we can define a clinically edematous region if brain extravascular water (BEW) exceeds that value. Also, we could define a clinically edematous region if brain extravascular water (BEW) exceeds the higher limit of the range of normal water content values or if BEW exceeds a selected value from within the range of normal water content values. In the example of FIG. 4, the patient course traversed three phases over 6 days: (Phase 1) a rapid increase in edema (i.e.: BEW) with a concomitant decrease in perfusion, presumably due to increased intracranial pressure with brain swelling; (Phase 2) an initial reduction in edema and sustained low perfusion, presumably because swelling continued to compromise flow; and (Phase 3) a continued reduction in edema at a rate similar as in Phase 2 with improvement in perfusion, presumably because reduced swelling enabled increased flow. This third phase is of interest because the reduction in extravascular water was offset with an increase in intravascular water that kept total brain water (i.e., thermal conductivity) relatively constant. In a clinical setting, this data would be available to the clinical team in real time for evaluation of brain water content and its constituent components, allowing for a more rapid response to a patient's condition. In this example (Phase 3), the ability to resolve total brain Water into its components, brain intravascular water (BIW) and brain extravascular water (BEW), helps clinicians confirm the continued progressive impact of the therapy to reduce edema (which is associated with BEW and not BIW) in spite of the relatively constant total brain water (BEW+BIW).

FIG. 1B shows the same relationship model as FIG. 1A wherein the patient-specific measured values for conductivity (k) and perfusion ($\omega$) are respectively 5.60 mw/cm-° C. and 30 ml/100 g-min. The perfusion coefficient of thermal conductivity ($m_\omega$) is plotted as the downwardly sloped line (slope=0.005) intersecting the conductivity axis at the point of measured conductivity (i.e.: the conductivity value of 5.60 mw/cm-° C.). The intercept of the sloped line representing the perfusion coefficient of thermal conductivity ($m_\omega$=0.005) and the ordinate line representing the measured perfusion value (30 ml/100 g-min) determines a second (i.e.: computed) value of conductivity of 5.45 mw/cm-° C. The measured conductivity of 5.60 mw/cm-° C. corresponds to the total brain water (BW) value of 85%; the calculated conductivity of 5.45 mw/cm-° C. corresponds to the brain extravascular water (BEW) value of 81.25%. To obtain the value for edema corresponding to the patient's current assessment (i.e.: measured k=5.60; measured co=30) a value selected from the normal range of BEW values (the normal range being shown in FIG. 1B as 67%-73%) is subtracted from the BEW value of 81.25%. In the example of FIG. 1B the value selected from the normal range is the upper limit of the normal range or 73.00%. The resulting edema value is the difference between 81.25% and 73.00% or 8.25%.

The above described determination of brain extravascular water utilizes a population-based perfusion coefficient of thermal conductivity. Perfusion and conductivity data gained in use of the edema monitor can be the basis of a real-time reassessment of the perfusion coefficient of thermal conductivity to develop a patient-specific perfusion coefficient or to fine tune the population-based perfusion coefficient. Enhanced perfusion coefficient values can form the basis of a revised and, in some circumstances, improved algorithm.

Figure 5:
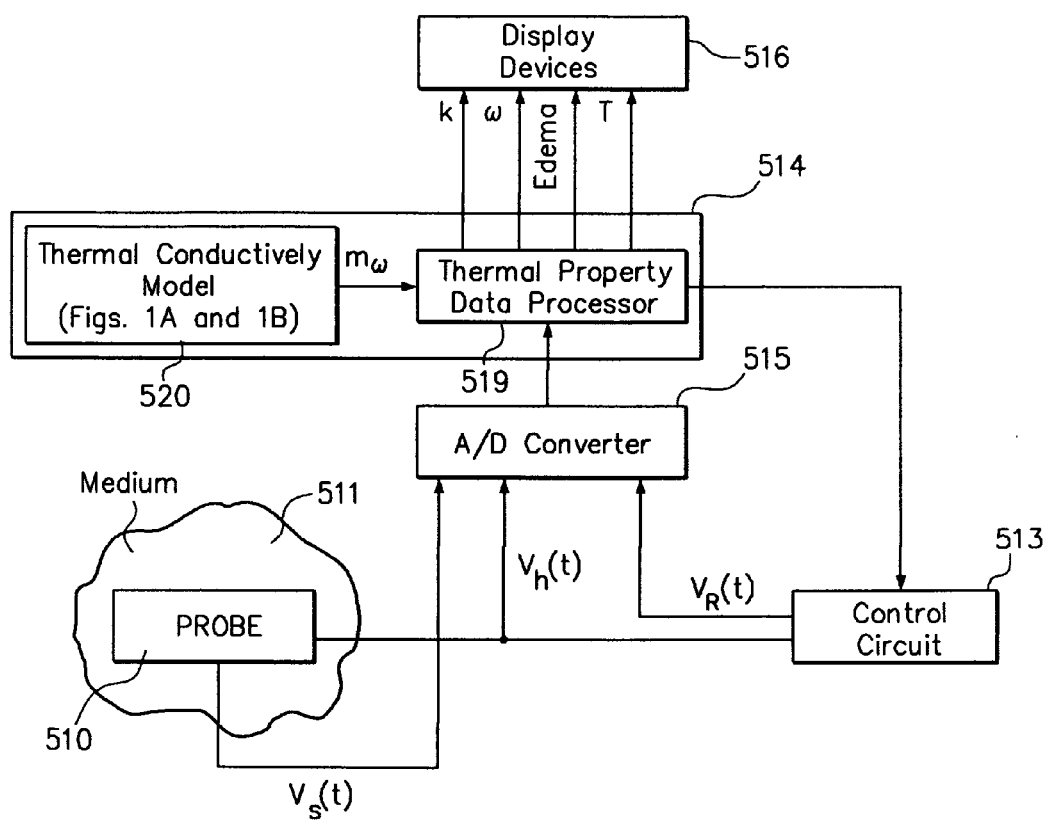
FIG. 5 is a block diagram of one example of a system in which the disclosed techniques can be used.

This invention can be implemented by use of a system such as that illustrated schematically in FIG. 5. As explained in the patents referenced above and illustrated by FIG. 5, a probe 510 is immersed in a medium (e.g.: tissue) 511 and energized; the energized probe is heated by a heater voltage $V_h(t)$ supplied via control circuit 513. The sensed voltage $V_s(t)$ from probe 510 is supplied to A/D converter 515 for input to a data processor 514 in digital form for suitable processing in order to determine k (intrinsic thermal conductivity), α (diffusivity), and ω (flow rate or perfusion). The values may be displayed in a display device 516.

The system incorporates the mathematical model described herein and exemplified by FIGS. 1A and 1B. The data processor 514 includes the thermal property data processor 519 and thermal conductivity model 520. The thermal property data processor 519 receives input from the thermal conductivity model 520 (corresponding to the examples of FIGS. 1A and 1B) to solve the above expressions 7, 8 and 9. The data processor 514 computes brain intravascular water (BIW) from the measured values for tissue conductivity (6.0 $m_\omega$/cm-° C. in the example of FIG. 1A) and perfusion (40% in the example of FIG. 1A).

Figure 6:
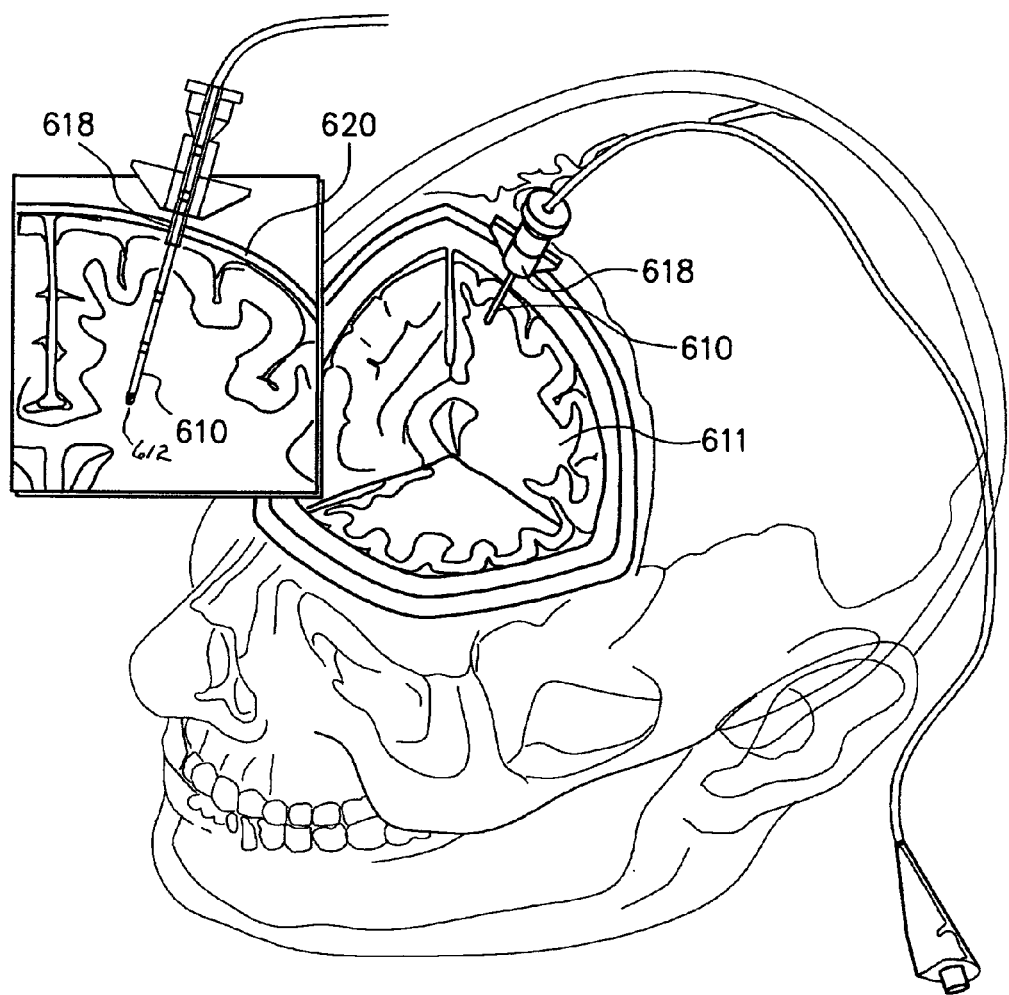
FIG. 6 shows a thermal probe located in the brain of a subject.

Viewing FIG. 6, a thermal probe 610 (e.g.: thermistor) is introduced into the cranium and into the brain tissue 611 via a burr hole through the skull 620. It is held in place by a cranial bolt 618.

Referring to FIG. 5, the probe 510 (which may be a self-heating thermistor) is immersed in a volume of tissue 511 and heated by a heater voltage $V_h(t)$ supplied via power source and control circuit 513. The temperature of the probe (i.e.: thermistor) is rapidly raised to a predetermined level above its initial equilibrium temperature, thus above the baseline temperature of the surrounding tissue, by the power source and control circuit 513. The heated probe causes the temperature of the surrounding volume of tissue to rise. The volume of tissue surrounding the probe 510 in which the temperature of the tissue is elevated to any substantial extent by the heated probe is considered the measurement field. The rate at which heat is transferred from the probe 510 is a function of the effective thermal conductivity of the tissue. The power used or dissipated in the probe 510 to maintain a predetermined elevated temperature level thus is also a function of the effective thermal conductivity of the surrounding tissue. The effective thermal conductivity of living tissue has two principal components, intrinsic thermal conductivity (k) of the tissue and tissue perfusion (ω) (i.e.: the effect of convection in the tissue). Intrinsic thermal conductivity of tissue is a function of tissue water content. Therefore the rate of heat transfer from the probe 510 is also a function of tissue water content. The voltage $V_h(t)$ across the probe 510 provides a parameter from which a determination of the effective thermal conductivity is made. The sensed voltage $V_s(t)$ from probe 510 is supplied to A/D converter 515 for input to a data processor 514 in digital form suitable for processing. In the data processor 514 the thermal effect of intrinsic thermal conductivity (k) and the thermal effect of perfusion (ω) are separated and determined. The determined values may be displayed in a display device 516. The intrinsic thermal conductivity value is used in the calculation of tissue water content.

In the data processor 514, as mentioned above, the thermal property data processor 519 receives input from the thermal property model 520 to solve expressions 7, 8 and 9. The data processor 514 computes brain total water (BW) from the measured value of conductivity (k) and brain intravascular water (BIW) from the measured values of conductivity (k) and perfusion (ω) and the perfusion coefficient of thermal conductivity ($m_\omega$). (See FIG. 1A or FIG. 1B.) Brain extravascular water (BEW) is the difference between the computed value of brain total water (BW) and the computed value of brain intravascular water (BIW). A value for edema is obtained by deducting from the resulting value for brain extravascular water (BEW) a selected tissue water content value within the normal range of tissue water values. The value for edema is displayed on the display device 516.

In the herein described embodiments for measuring edema the mathematical model is that described above, particularly that embodied by expressions (7), (8) and (9). The mathematical model is implemented in the data processor 514 to determine brain intravascular water (BIW) and brain extravascular water (BEW) components of total brain water (BW), which values along with the calculated value of edema may be displayed in the display device 516. The significance of BIW, BEW and BW is illustrated in the plots of FIG. 1A. In that example the patient's current assessment is shown at a measured conductivity (k) value of 6.0 mw/cm-° C. and a measured perfusion (ω) value of 40 ml/100 g-min. The measured conductivity value of 6.0 corresponds to total brain water (BW) of approximately 95%. The perfusion coefficient of thermal conductivity ($m_\omega$) is plotted as a downwardly sloped line intersecting the conductivity axis at the point of measured conductivity (i.e.: the value of 6.0). The locus of the intercept of the sloped line (i.e.: the perfusion coefficient of thermal conductivity, $m_\omega$) with the line representing the measured perfusion value (i.e.: the value of 40) defines the computed value of thermal conductivity. The computed value of thermal conductivity is indicative of the separate brain intravascular water and brain extravascular water components of total brain water. In FIG. 1A the computed value of thermal conductivity is 5.80 mw/cm-° C.; that value corresponds to a brain extravascular water value of 90% and a brain intravascular water value of 5% (total brain water of 95% minus brain extravascular water of 90%). Edema is the portion of brain extravascular water in excess of the normal levels of brain extravascular water. The normal level of brain extravascular water is shown on the plot of FIG. 1A as 69.6%±1%. Using the value of 69.6% for normal extravascular water, edema in the illustrated instance is 20.4% (brain extravascular water of 90% minus normal extravascular water of 69.6%). (The value for normal extravascular water can be any value selected from the range of normal values, shown in FIG. 1A as 67%-73%).

In FIGS. 1A and 1B the slope of the plot representing the perfusion coefficient of thermal conductivity ($m_\omega$) is constant and its intercept with the conductivity axis is located at the measured value of conductivity. Accordingly, with changes in measured values of conductivity and measured values of perfusion the changed values of total brain water, brain intravascular water and brain extravascular water are reflected. Empirical data (FIGS. 2B and 2B) suggests a linear fit for the perfusion coefficient of thermal conductivity. This is reflected in linear slope of the plot of the perfusion coefficient of thermal conductivity in FIGS. 1A and 1B. It is possible that more data possibly could introduce a small non-linearity in the fit and thus in the plot.

Figure 7:
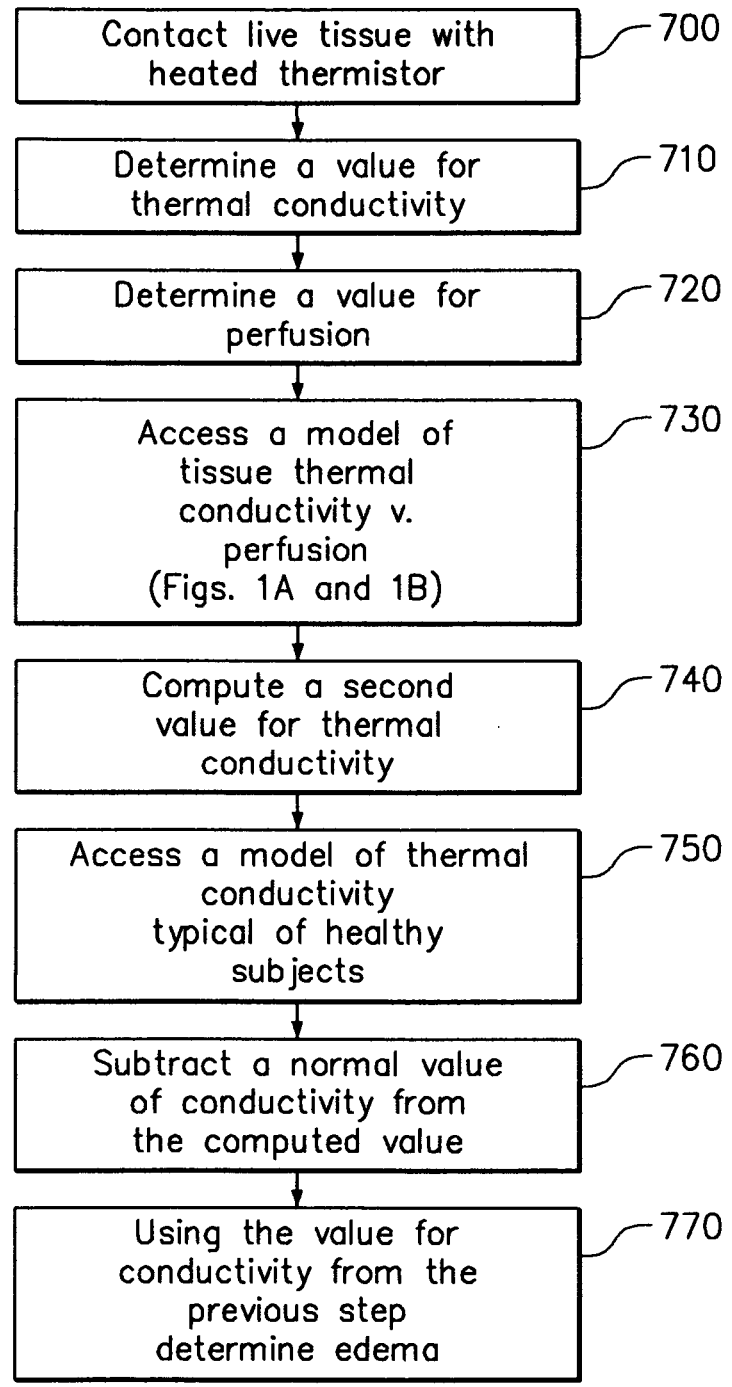
FIG. 7 is a flow chart of one embodiment of a method for determining edema according to the present invention.

In one embodiment of this invention the method of quantifying edema includes the steps shown in the flow chart of FIG. 7. Living tissue is contacted with the thermistor and the thermistor is heated (700) to a level above the base temperature of the tissue. This causes the temperature of a volume of tissue surrounding the thermistor to rise. The rate at which heat dissipates from the thermistor is a function of the perfusion in the tissue and the thermal conductivity of the tissue. The thermal conductivity of the tissue is determined (710) and tissue perfusion is determined (720) as a function of the temperature rise of the thermistor and the power required to heat the thermistor. The model of tissue conductivity as a function of perfusion, referenced above in connection with FIGS. 1A and 1B, is accessed (730) and the data processor computes (740) a second, calculated, value of conductivity as a function of measured values of thermal conductivity and perfusion, the second value of conductivity being indicative of the extravascular water content. (Viewing FIGS. 1A and 1B, the second value of conductivity is the value of conductivity at the intercept of the vertical measured perfusion line with the sloped plot of the perfusion coefficient of thermal conductivity.) A normal value of thermal conductivity, that characteristic of a healthy subject, is accessed (750) and subtracted from the second conductivity value (760) to obtain the conductivity associated with patient edema (770).

In one embodiment a method for quantifying edema in living tissue of a subject comprises the steps of:
contacting living tissue with a thermal sensor at a site where edema is to be quantified;
energizing the thermistor to cause the temperature of a volume of tissue to rise;
as a function of the power used to energize the thermistor and the temperature rise of the thermistor determining thermal conductivity of the volume of tissue and perfusion in the volume of tissue;
accessing a model relating the perfusion coefficient of thermal conductivity to the determined tissue conductivity and the determined tissue perfusion;
determining a second value of conductivity indicative of tissue extravascular water using the determined value of conductivity, the determined value of perfusion and the conductivity model;
accessing a value of conductivity typical of a healthy subject; and
computing a value indicative of edema as a function of the difference between the second value of conductivity and the value of conductivity typical of a healthy subject.

The invention is not to be deemed as limited to the herein described embodiments except as defined by the following claims.

The invention claimed is:

1. A system for determining a value for tissue extravascular water in living tissue comprising:
a thermistor probe adapted to be inserted into living tissue for detecting in the volume of tissue surrounding the thermistor probe a thermal conductivity value indicative of the total water content of the volume of tissue;
means for determining in the volume of tissue a value indicative of perfusion in the volume of tissue as a function of the detected thermal conductivity value;
a model of the relationship in living tissue of perfusion and thermal conductivity obtained from multiple measurements of thermal conductivity and perfusion in a population of living subjects;
means for calculating a second value for thermal conductivity indicative of tissue intravascular water in the volume of tissue using the detected thermal conductivity value, the determined value indicative of perfusion and a value representing the relationship of thermal conductivity in living tissue to perfusion in living tissue provided by said model; and
means for determining a value indicative of tissue extravascular water in the volume of tissue using the detected thermal conductivity value and the calculated second value for thermal conductivity.

2. A method for determining a value for tissue extravascular water in a volume of living tissue comprising the steps of:
introducing a thermistor probe into living tissue;
heating the thermistor probe to a temperature above the baseline temperature of the surrounding tissue by means of a control circuit having a power source for energizing the thermistor probe,
as a function of the power used by the heating step detecting in the volume of tissue a value for thermal conductivity indicative of the total tissue water in the volume of tissue;
detecting in the volume of tissue a value for perfusion in the volume of tissue as a function of the detected value for conductivity in the volume of tissue; and
calculating a second value for thermal conductivity indicative of tissue extravascular water in the volume of tissue using the detected value for thermal conductivity, the detected value for perfusion and a value for the relationship in living tissue between thermal conductivity and perfusion provided by an empirically developed model of the relationship of tissue perfusion values and tissue thermal conductivity values created from multiple measurements in living tissue of thermal conductivity and perfusion in a population of subjects.

3. A system for determining a value for tissue extravascular water in a volume of living brain tissue of a subject comprising:
a thermistor probe for insertion into living brain tissue;
a control circuit having a power source for energizing the thermistor probe to raise the temperature of tissue surrounding the thermistor probe;
an empirical model of the relationship of perfusion in living brain tissue and thermal conductivity in living brain tissue; and
means responsive to the power required to heat the thermistor probe and a value for the relationship of perfusion in living brain tissue and thermal conductivity in living brain tissue provided by the model for determining a value indicative of tissue extravascular water in the tissue surrounding the thermistor probe.

4. A system according to claim 3 wherein the empirical model is obtained from multiple measurements of thermal conductivity and perfusion in living brain tissue in a population of subjects.

* * * * *